United States Patent [19]

Bauer

[11] E Re. 28,575

[45] Reissued Oct. 21, 1975

[54] INDICATOR FOR DETECTING HYDROGEN PEROXIDE AND PEROXIDATIVE COMPOUNDS CONTAINING ALPHA NAPHTHOFLAVONE

[75] Inventor: Robert Bauer, Bristol, Ind.

[73] Assignee: Miles Laboratories, Inc., Elkhart, Ind.

[22] Filed: Apr. 8, 1974

[21] Appl. No.: 459,126

Related U.S. Patent Documents

Reissue of:

[64] Patent No.: 3,654,180
Issued: Apr. 4, 1972
Appl. No.: 119,926
Filed: Mar. 1, 1971

[52] U.S. Cl. ..... 252/408; 195/103.5 C; 23/253 TP; 23/230 B; 8/1 R

[51] Int. Cl.[2] ..... G01N 31/22; G01N 33/16

[58] Field of Search ..... 252/408; 8/1 R; 23/230 B, 23/253 TP; 195/103.5 C

[56] References Cited

UNITED STATES PATENTS

| | | | |
|---|---|---|---|
| 2,799,660 | 7/1957 | Nicholls | 252/408 |
| 3,066,081 | 11/1962 | Rorem | 195/103.5 X |
| 3,092,465 | 6/1963 | Adams | 23/253 |
| 3,183,173 | 5/1965 | Oakes | 23/230 |
| 3,814,668 | 6/1974 | Blake | 23/253 TP X |

*Primary Examiner*—Benjamin R. Padgett
*Assistant Examiner*—David Leland
*Attorney, Agent, or Firm*—Andrew L. Klawitter

[57] ABSTRACT

Alpha naphthoflavone is an excellent indicator for detecting hydrogen peroxide and peroxidative compounds such as hemoglobin. When formulated with either a peroxidative active compound or a peroxide, this indicator provides a very sensitive chromogenic response to the presence of said constituents in aqueous fluids.

7 Claims, No Drawings

INDICATOR FOR DETECTING HYDROGEN PEROXIDE AND PEROXIDATIVE COMPOUNDS CONTAINING ALPHA NAPHTHOFLAVONE

Matter enclosed in heavy brackets [ ] appears in the original patent but forms no part of this reissue specification; matter printed in italics indicates the additions made by reissue.

BACKGROUND OF THE INVENTION

The determination of glucose in urine is important since this test is employed to detect diabetes. Procedures for the detection of sugar in urine are well known in clinical chemistry. One such procedure utilizes Benedict's copper reduction test, another employs a self heating alkaline copper reduction test in tablet form, while still another test depends solely on the action of enzymes. The diagnostic composition in most glucose tests comprises essentially glucose oxidase, peroxidase and an indicator which is oxidized by hydrogen peroxide and undergoes a color reaction during such oxidation. Typical indicators employed in the past include o-tolidine, benzidine dianisidine and 27-diaminofluorene.

It is well known that glucose oxidase catalyzes the aerobic oxidation of glucose to gluconic acid and hydrogen peroxide. However in the presence of iodide, $H_2O_2$ oxidizes the iodide to free iodine which produces a color change in the indicator. The color change produced is accurately indicative of the amount of $H_2O_2$ present as well as of the glucose content of the fluid being tested. Molybdates merely accelerate the oxidation of iodide to free iodine. Since some of the indicators previously used are toxic it has spurred a search for more suitable replacements which will give satisfactory results in detecting $H_2O_2$ generally and more specifically in detecting glucose in urine or blood. If desired such indicators can be used to detect peroxidase as well as peroxidative-active substances such as hemoglobin in blood or urine.

SUMMARY OF THE INVENTION

This invention is predicated upon the discovery that α-naphthoflavone can be used as an indicator dyestuff in formulations containing either peroxide or a peroxidative active compound when the peroxidative active compound catalyzes the oxidation of the indicator by the peroxide. Said indicator has the formula

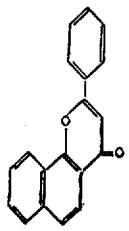

and is known chemically as 2-phenyl-4H naphtho [1,2-b]pyran-4-one.

Although the test system may comprise the reagent composition in the form of a tablet, powder or solution, it is preferable to affix said composition on bibulous base materials or carriers such as strips of filter paper by dissolving the components in a suitable solvent, impregnating the strips with the resulting solution and drying the impregnated test strips. Details of the compositions contemplated are set forth in the following examples.

DESCRIPTION OF THE PREFERRED EMBODIMENTS

Example 1

A composition was prepared by mixing the following components in the volumes indicated below:

Glucose oxidase—5 ml. of an aqueous solution containing 1000 International units per ml.
Peroxidase—1 ml. of an aqueous solution containing 2 mg./ml.
Potassium iodide—160 mg.
Polyvinylalcohol—2 ml. of a 10% aqueous solution.
Dioctyl sodium sulfosuccinate—1 ml. of a 1% aqueous solution.
Tris-glutamate buffer—2 ml. of a 0.2 M solution of pH 7.
α-Naphthoflavone—6 ml. of a 0.5% ethanol solution.
Water—5 ml.

Example 2

Another composition was prepared employing no peroxidase as shown below:

Glucose oxidase—3 ml. of an aqueous solution containing 1000 International units/ml.
Potassium iodide—80 mg.
Ammonium molybdate—160 mg.
Sodium phosphate buffer—3 ml. of a 1 M solution of pH 6.
α-Naphthoflavone—1 ml. of a 0.5% ethanol solution.
Water—5 ml.

Porous paper strips about ½ inch wide and 3 inches long were dipped into the above compositions respectively so that about one-half inch of each strip at one end was completely impregnated. The strips were then dried at 100° C. for 10 minutes. If desired, other porous materials such as wood or plastics can be used as carriers. When contacted with urine containing glucose, such test strips give a positive reaction in 1 minute or less as evidenced by the change in color of the indicator from colorless to blue. The formation of color depends upon the liberation of free iodine from the iodide by the action of hydrogen peroxide. When dipped into urine containing no glucose, the strips show no color change. The intensity of the blue color is enhanced in the presence of polyvinyl alcohol. When molybdates and iodides are substituted for the peroxidase, the α-naphthoflavone minimizes the inhibiting effects of acetoacetate which is also an iodine receptor. It was found that when the strips containing the composition of Example 2 were dipped into a 1% aqueous solution of glucose containing 0.1% by weight of acetoacetate they began to change from colorless to blue in 30 seconds and the blue color gradually intensified, whereas strips containing o-tolidine started to show a blue color at 1.5 minutes with very little increase in color intensity even after 5 minutes' contact with the same glucose solution.

Example 3

A first solution was prepared containing 1.5 grams of carrageen, 15 grams of polyvinylpyrrolidone, 15 ml. of ethanol and 192 ml. of water.

A second solution was prepared containing 9.24 grams of citric acid, 40.79 grams of sodium citrate and 124.8 ml. of water.

A third solution was prepared containing 4.5 grams of a maleic anhydride-methylvinylether copolymer, 1.5 grams of sodium lauroyl sarcosinate and 105 ml. of water.

Still, a fourth solution was prepared containing 0.5 gram of peroxidase and 76 ml. of an aqueous solution of glucose oxidase containing 1,000 international units per ml. of water.

A composition for detecting $H_2O_2$ and glucose was thereafter prepared containing 9 ml. of a 0.5% ethanol solution of α-naphthoflavone, 0.73 gram of potassium iodide, 9 ml. of ethanol, 5.5 ml. of water, 34.5 ml. of the first solution above, 20.8 ml. of the second solution above, 17.5 ml. of the third solution above and 7.6 ml. of the fourth solution previously prepared. Bibulous paper strips were dipped in said solution and then dried for 10 minutes at 100° C. These strips readily turned from colorless to blue when contacted with urine containing lucose and the blue color increased with the glucose concentration. Such strips also change from colorless to blue when a drop of blood-containing urine and a drop of 3% hydrogen peroxide solution is applied thereto.

In addition to the compositions set forth in the foregoing examples, it was found that the amount of indicator employed could be varied from 0.05% to 0.30% by weight in such compositions whereas the glucose oxidase concentration could vary from 40 to 300 International units per ml. of peroxidase from 0.01% to 0.05%, the sodium iodide from 0.25% to 1.5%, the ammonium molybdate from 0.1% to 1.5%, and the polyvinyl alcohol from 0.2% to 2% by weight of ultimate mix at a pH of from 4 to 7.

What is claimed is:

1. In a composition for detecting hydrogen peroxide or peroxidative active compounds utilizing the catalytic oxidation of an indicator *system* [dyestuff] by hydrogen peroxide in the presence of the peroxidative active compound, the improvement which comprises the use of α-naphthoflavone *in combination with a water soluble iodide salt* as the indicator *system* [dyestuff.]

2. A composition as claimed in claim 1 in which α-naphthoflavone is present in about 0.05% to 0.30% by weight of said composition.

3. A composition as claimed in claim 1 in which the peroxidative active compound is selected from the group consisting of peroxidase, hemoglobin and molybdate.

4. A composition as claimed in claim 3 in which the molybdate is present in about 0.1% to 1.5% by weight of said composition.

5. A composition as claimed in claim 3 in which the peroxidase is present in about 0.01% to 0.05% by weight of said composition.

[6. A composition as claimed in claim 1 which additionally contains iodide.]

7. A composition as claimed in claim *1* [6] in which the *water soluble* iodide *salt* is present in about 0.25% to 1.5% by weight of said composition.

8. A composition for detecting glucose in aqueous fluids which comprises glucose oxidase, a peroxidative active material, *a water soluble iodide salt*, and α-naphthoflavone.

* * * * *